(12) United States Patent
Glasser et al.

(10) Patent No.: US 11,512,811 B2
(45) Date of Patent: Nov. 29, 2022

(54) SYSTEM AND METHOD FOR DETECTING A LUBRICANT-OUT CONDITION IN AN AIRCRAFT GEARBOX

(71) Applicant: SIKORSKY AIRCRAFT CORPORATION, Stratford, CT (US)

(72) Inventors: Adam R. Glasser, Wolcott, CT (US); Dwaine Wint, New Haven, CT (US); John J. Baldyga, Wallingford, CT (US); Michael F. Mullen, Cheshire, CT (US); David M. Lutian, Milford, CT (US); Lindsey McKan, Milford, CT (US)

(73) Assignee: SIKORSKY AIRCRAFT CORPORATION, Stratford, CT (US)

( * ) Notice: Subject to any disclaimer, the term of this patent is extended or adjusted under 35 U.S.C. 154(b) by 855 days.

(21) Appl. No.: 16/316,766

(22) PCT Filed: Jul. 11, 2017

(86) PCT No.: PCT/US2017/041485
§ 371 (c)(1),
(2) Date: Jan. 10, 2019

(87) PCT Pub. No.: WO2018/013529
PCT Pub. Date: Jan. 18, 2018

(65) Prior Publication Data
US 2019/0154200 A1    May 23, 2019

Related U.S. Application Data

(60) Provisional application No. 62/361,076, filed on Jul. 12, 2016.

(51) Int. Cl.
*F16N 29/02*    (2006.01)
*B64D 45/00*    (2006.01)
(Continued)

(52) U.S. Cl.
CPC .............. *F16N 29/04* (2013.01); *B64C 27/14* (2013.01); *B64C 27/16* (2013.01); *B64D 45/00* (2013.01);
(Continued)

(58) Field of Classification Search
CPC . B64D 45/00; B64D 2045/0085; F16N 29/04; F16H 57/0449; F01M 1/20
(Continued)

(56) References Cited

U.S. PATENT DOCUMENTS 3,366,942 A * 1/1968 Deane .................. G01P 13/006
                                                   73/204.11
4,354,183 A * 10/1982 Weeks ................. F16C 33/1085
                                                   374/E1.005
(Continued)

FOREIGN PATENT DOCUMENTS

DE    29611668 U1    10/1996
EP    2584323 B1    4/2013
(Continued)

OTHER PUBLICATIONS

"Aerospace Flow Sensors", FCI© : Fluid Components International LLC, 2016, obtained from: http://www.fluidcomponents.com/Aerospace/Products/FlowSensors/A_ProdFlow.asp, date of retrieval: May 18, 2016, 1 page.
(Continued)

*Primary Examiner* — Michael R Mansen
*Assistant Examiner* — Mark K Buse
(74) *Attorney, Agent, or Firm* — Michael Best & Friedrich LLP

(57) ABSTRACT

A gearbox includes a housing including a lubricant reservoir, at least one gear system arranged in the housing, at least one lubricant delivery passage operable to direct a flow of lubricant from a lubricant reservoir onto the at least one gear (Continued)

system, at least one lubricant return passage operable to guide the flow of lubricant to the lubricant reservoir, and a lubricant-out sensor fluidically connected to the at least one lubricant return passage. The lubricant-out sensor is operable to detect a non-pressure based parameter of the lubricant.

15 Claims, 2 Drawing Sheets

(51) Int. Cl.

| | | |
|---|---|---|
| F16H 57/04 | (2010.01) | |
| F16N 29/04 | (2006.01) | |
| B64C 27/14 | (2006.01) | |
| F16N 29/00 | (2006.01) | |
| F16N 7/00 | (2006.01) | |
| B64C 27/16 | (2006.01) | |
| G01N 33/28 | (2006.01) | |
| G01F 23/22 | (2006.01) | |
| G01F 23/24 | (2006.01) | |

(52) U.S. Cl.
CPC ............ *F16H 57/0457* (2013.01); *F16N 7/00* (2013.01); *F16N 29/00* (2013.01); *F16N 29/02* (2013.01); *G01N 33/2888* (2013.01); *B64D 2045/0085* (2013.01); *F16N 2250/08* (2013.01); *F16N 2250/18* (2013.01); *G01F 23/22* (2013.01); *G01F 23/24* (2013.01); *G01F 23/246* (2013.01)

(58) Field of Classification Search
USPC ........................................................ 324/668
See application file for complete search history.

(56) References Cited

U.S. PATENT DOCUMENTS

| | | | |
|---|---|---|---|
| 4,647,919 A * | 3/1987 | Wright | G01F 1/698 340/606 |
| 5,344,101 A | 9/1994 | Francois | |
| 5,672,112 A | 9/1997 | Sbabo | |
| 6,433,560 B1 * | 8/2002 | Hansen | G01F 23/266 324/668 |
| 6,666,300 B2 * | 12/2003 | Varailhon | F16H 57/045 184/6.12 |
| 7,000,466 B2 * | 2/2006 | Larson | G01F 1/6986 73/290 R |
| 7,137,590 B2 | 11/2006 | Sandrart et al. | |
| 8,826,774 B1 * | 9/2014 | Craig | F16H 57/027 74/606 R |
| 9,260,186 B1 | 2/2016 | Van Der Westhuizen | |
| 9,267,403 B2 | 2/2016 | Huillet et al. | |
| 2004/0056772 A1 * | 3/2004 | Sammataro | F16N 29/04 374/E11.006 |
| 2010/0025159 A1 * | 2/2010 | Gmirya | F16N 17/00 184/6.4 |
| 2012/0067671 A1 * | 3/2012 | Sammataro | F16N 29/04 384/445 |
| 2014/0026702 A1 * | 1/2014 | Sinusas | F16H 57/0443 74/467 |
| 2014/0030110 A1 * | 1/2014 | Sinusas | F16N 7/363 416/243 |
| 2014/0097044 A1 * | 4/2014 | Mullen | F16N 39/00 184/6.12 |
| 2015/0198578 A1 | 7/2015 | Worden et al. | |
| 2018/0051793 A1 * | 2/2018 | Ture | B64D 45/00 |

FOREIGN PATENT DOCUMENTS

| | | |
|---|---|---|
| KR | 20020045722 A | 6/2002 |
| RU | 2108510 C1 | 4/1998 |
| WO | 2015092243 A1 | 6/2015 |
| WO | 2016076945 A1 | 5/2016 |

OTHER PUBLICATIONS

Notification of Transmittal of the International Search Report and the Written Opinion of the International Searching Authority, or the Declaration; PCT/US2017/041485; dated Oct. 2, 2017; 15 pages.
Machine translation for DE29611668; Publication Date Oct. 17, 1996; Inventor Haehne et al. (pp. 1-9).
European Search Report for European Application No. 17828276.0; Report dated Feb. 19, 2020 (pp. 1-13).

* cited by examiner

SYSTEM AND METHOD FOR DETECTING A LUBRICANT-OUT CONDITION IN AN AIRCRAFT GEARBOX

CROSS REFERENCE TO RELATED APPLICATIONS

This application is a National Stage application of PCT/US2017/041485, filed Jul. 11, 2017, published Jan. 18, 2018 as WO 2018/013529 which claims the benefit of U.S. Provisional Application No. 62/361,076, filed Jul. 12, 2016, both of which are incorporated by reference in their entirety herein.

BACKGROUND

Exemplary embodiments pertain to the art of aircraft and, more particularly, to a system and method for detecting a lubricant-out condition in an aircraft gearbox.

Aircraft includes a number of systems that promote proper flight conditions. Failure of such a system may lead to an undesirable or unplanned landing. Accordingly, manufactures design aircraft with a capability to maintain flight for a period of time following a system failure. The period of time may vary for particular aircraft. Military aircraft should be capable of sustained safe flight for a period of time following a ballistic impact to the system.

BRIEF DESCRIPTION

Disclosed is a gearbox including a housing including a lubricant reservoir, at least one gear system arranged in the housing, at least one lubricant delivery passage operable to direct a flow of lubricant from a lubricant reservoir onto the at least one gear system, at least one lubricant return passage operable to guide the flow of lubricant to the lubricant reservoir, and a lubricant-out sensor fluidically connected to the at least one lubricant return passage. The lubricant-out sensor is operable to detect a non-pressure based parameter of the lubricant.

In addition to one or more of the features described above or below, or as an alternative, further embodiments could include wherein the lubricant-out sensor includes a sensing element extending into the at least one lubricant return passage.

In addition to one or more of the features described above or below, or as an alternative, further embodiments could include wherein the lubricant-out sensor comprises a temperature sensor, wherein the non-pressure based parameter comprises lubricant temperature.

In addition to one or more of the features described above or below, or as an alternative, further embodiments could include wherein the lubricant-out sensor comprises a conductivity sensor, wherein the non-pressure based parameter comprises lubricant conductivity.

In addition to one or more of the features described above or below, or as an alternative, further embodiments could include wherein the lubricant-out sensor comprises a combination sensor operable to sense at least two non-pressure based parameters of the lubricant.

In addition to one or more of the features described above or below, or as an alternative, further embodiments could include wherein the at least two non-pressure based parameters include temperature and conductivity.

In addition to one or more of the features described above or below, or as an alternative, further embodiments could include wherein the gearbox comprises a splash lubricated gearbox.

Also disclosed is a rotary wing aircraft including an airframe having an extending tail, at least one engine operatively supported to the airframe, a main rotor assembly operatively coupled to the at least one engine, a tail rotor assembly mounted at the extending tail, and at least one gearbox operatively connecting the at least one engine and the tail rotor assembly. The gearbox includes a housing including a lubricant reservoir, at least one gear system arranged in the housing, at least one lubricant delivery passage operable to direct a flow of lubricant from a lubricant reservoir onto the at least one gear system, at least one lubricant return passage operable to guide the flow of lubricant to the lubricant reservoir, and a lubricant-out sensor fluidically connected to the at least one lubricant return passage. The lubricant-out sensor is operable to detect a non-pressure based parameter of the lubricant.

In addition to one or more of the features described above or below, or as an alternative, further embodiments could include wherein the lubricant-out sensor comprises a temperature sensor, wherein the non-pressure based parameter comprises lubricant temperature.

In addition to one or more of the features described above or below, or as an alternative, further embodiments could include wherein the lubricant-out sensor comprises a conductivity sensor, wherein the non-pressure based parameter comprises lubricant conductivity.

In addition to one or more of the features described above or below, or as an alternative, further embodiments could include wherein the lubricant-out sensor comprises a combination sensor operable to sense at least two non-pressure based parameters of the lubricant.

In addition to one or more of the features described above or below, or as an alternative, further embodiments could include wherein the at least two non-pressure based parameters include temperature and conductivity.

In addition to one or more of the features described above or below, or as an alternative, further embodiments could include wherein the gearbox comprises a splash lubricated gearbox.

Also disclosed is a method of determining an lubricant-out condition in a splash lubricated gearbox including a housing having an lubricant reservoir, at least one gear system arranged in the housing, at least one lubricant delivery passage operable to direct a flow of lubricant from a lubricant reservoir onto the at least one gear system, and at least one lubricant return passage operable to guide the flow of lubricant to the lubricant reservoir. The method includes sensing a non-pressure based parameter of the lubricant in the at least one lubricant return passage, and providing a lubricant-out warning based on the non-pressure based parameter of the lubricant.

In addition to one or more of the features described above or below, or as an alternative, further embodiments could include wherein sensing the non-pressure based parameter of the lubricant includes sensing at least one of lubricant temperature and lubricant conductivity.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Figure 1:
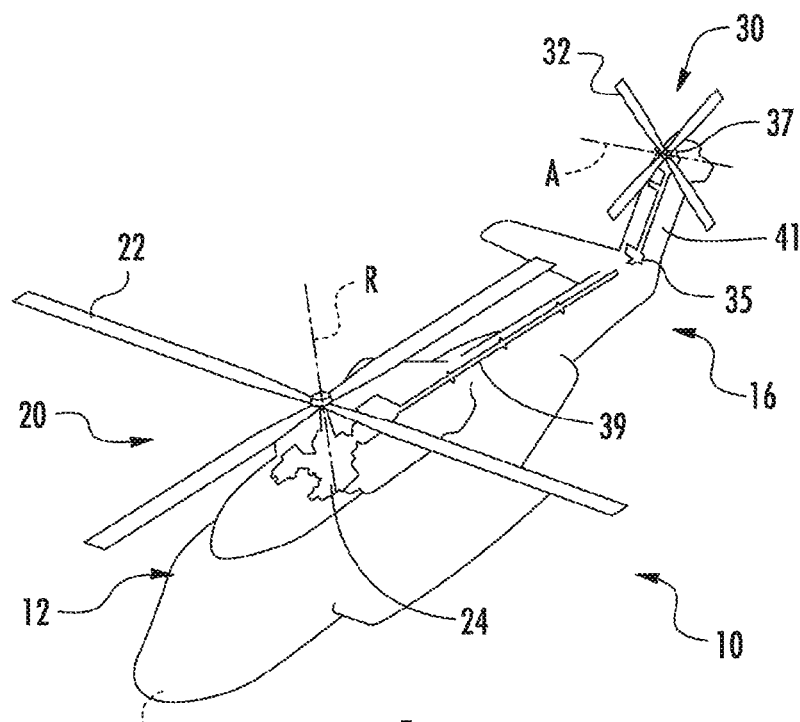
FIG. 1 is a schematic view of a rotary wing aircraft including a gearbox, in accordance with an exemplary embodiment.

FIG. 1 schematically illustrates a rotary wing aircraft 10 having an airframe 12 including a nose 14 and an extending tail 16. Airframe 12 supports a main rotor assembly 20 including a plurality of rotor blades, one of which is indicated at 22. Main rotor assembly 20 is driven by an engine 24 to rotate about a main rotor axis "R". Aircraft 10 also includes a tail rotor assembly 30 including a plurality of tail rotor blades 32. Tail rotor assembly 30 is mounted to extending tail 16 and operatively connected to engine 24. More specifically, tail rotor system 30 is connected to engine 24 through a first gearbox 35 and a second gearbox 37. A first driveshaft 39 mechanically links engine 24 and first gearbox 35. A second drive shaft 41 mechanically links first gearbox 35 with second gearbox 37. With this arrangement, engine 24 drives tail rotor blades 32 about a tail rotor axis "A". In the exemplary embodiment shown, tail rotor axis A is substantially perpendicular to main rotor axis R.

Although a particular helicopter configuration is illustrated and described in the disclosed embodiment, other configurations and/or machines, such as high speed compound rotary wing aircraft with supplemental translational thrust systems, dual counter-rotating or co-rotating coaxial rotor system aircraft, turbo-props, tilt-rotors and tilt-wing aircraft, as well as ground and sea vehicles may also benefit from the exemplary embodiments. Additionally, it is to be understood that the number and arrangement of gearboxes may vary.

Figure 2:
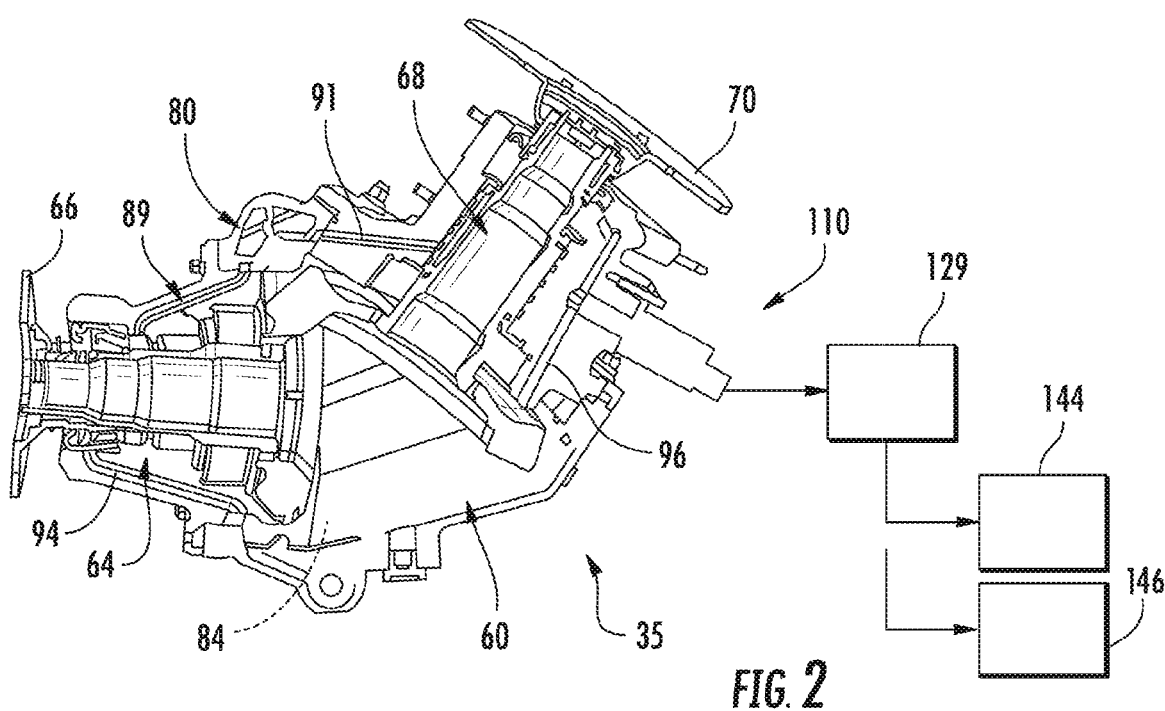
FIG. 2 is a partial cross-sectional view of the gearbox of FIG. 1, depicting an lubricant-out sensor, in accordance with an exemplary embodiment.
Figure 3:
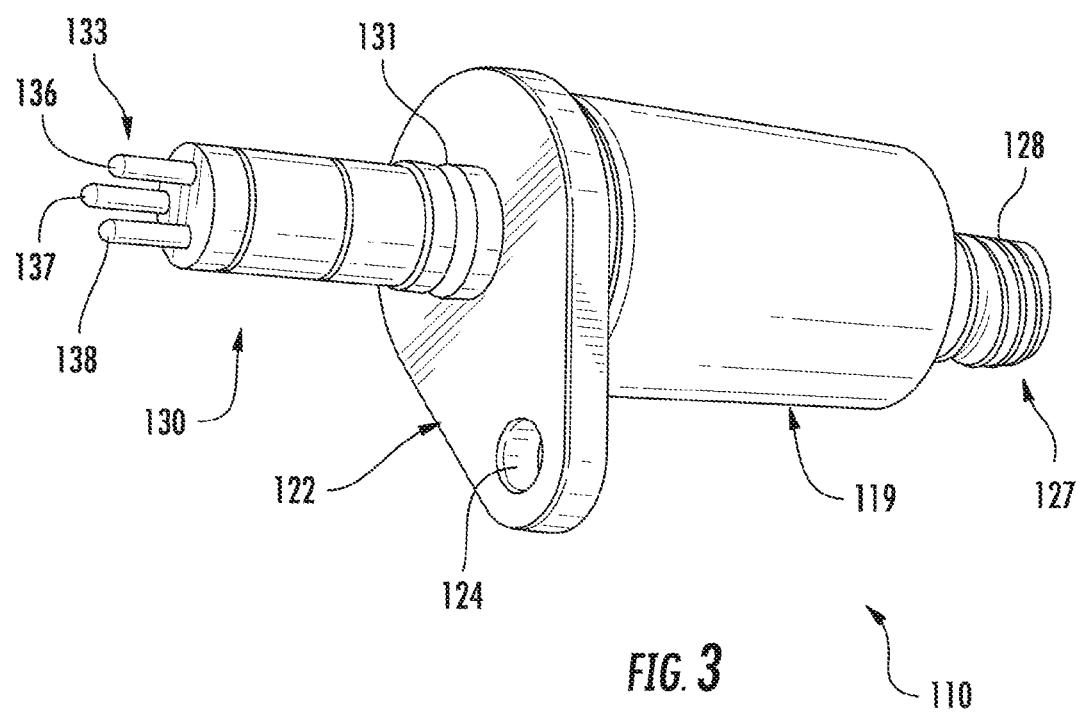
FIG. 3 depicts the lubricant-out sensor of FIG. 2.

Reference will now follow to FIG. 2 in describing first gearbox 35 with an understanding that second gearbox 37 may include similar structure. First gearbox 35 defines a splash lubricated gearbox. A splash lubricated gearbox should be understood to direct lubricant, typically oil, onto rotating components at ambient pressure. First gearbox 35 includes a housing 60 that supports an input gear system 64 having an input flange 66 coupled to first drive shaft 39 and an output gear system 68 having an output flange 70 coupled to second drive shaft 41. Input gear system 64 mechanically links with output gear system 68. First gearbox 35 also includes a lubricant delivery system 80 which may take the form of cups or the like coupled to input gear system 64, and/or output gear system 68.

Lubricant delivery systems 80 captures an amount of lubricant from a lubricant reservoir 84 and directs that lubricant onto rotating components of first gearbox 35 including input gear system 64 and output gear system 68. At least one first lubricant delivery passage 89 directs a flow of lubricant to input gear system 64 and at least one second lubricant delivery passage 91 delivers a flow of lubricant to output gear system 68. First gearbox 35 also includes at least one first lubricant return passage 94 that guides a flow of lubricant from input gear system 64 back to lubricant reservoir 84 and at least one second lubricant return passage 96 that guides a flow of lubricant from output gear system 68 back to lubricant reservoir 84.

In accordance with an aspect of an exemplary embodiment, first gearbox 35 includes a lubricant-out sensor 110 that senses a loss of lubricant based on a non-pressure based lubricant parameter. More specifically, as a splash lubricated system delivers lubricant without the aid of pressure, lubricant-out sensor 110 relies on other lubricant parameters, to determine a loss of lubricant situation. Lubricant-out sensor 110 includes a sensor body 119 having a mounting flange 122. Mounting flange 122 includes an opening 124 that receives a mechanical fastener (not separately labeled) that secures lubricant-out sensor 110 to first gearbox 35. Sensor body 119 includes a connector 127 having a plurality of threads 128 that operatively connects lubricant-out sensor 110 to a controller 129. While described in terms of a non-pressure parameter, it is understood that the sensor 110 could also be used in a pressurized system where a pressure switch also provides an alert to the pilot.

In further accordance with an exemplary aspect, lubricant-out sensor 110 includes a sensing member 130 that extends into first gearbox 35. In the exemplary embodiment shown, sensing member 130 extends into return passage 96. It is to be understood that sensing member 130 could extend into other passages that conduct lubricant including lubricant delivery passages and lubricant return passages. An O-ring 131 extends about sensing member 130 to provide a seal. Sensing member 130 may include a plurality of sensing elements 133 that extends into second lubricant return passage 96 so as to directly fluidically contact lubricant contained therein. The plurality of sensing elements 133 may include a first sensing element 136, a second sensing element 137 and a third sensing element 138. First sensing element 136 may represent a temperature sensing element and second and third sensing elements 137, 138 may represent conductivity sensing elements. Of course, it should be understood that all of the sensing elements may be similar, e.g., temperature sensing elements or conductivity sensing elements. It is to be understood that the number of sensing elements may vary. Thus, lubricant-out sensor 110 may take the form of a lubricant temperature sensor, a lubricant conductivity sensor, or a combination sensor detecting both lubricant temperature and lubricant conductivity sensor.

Lubricant-out sensor 110 compares a first signal from first sensing element 136, a second signal from second sensing element 137 and a third signal from third sensing element 138 to detect two non-pressure based parameters indicating a lack of oil. If only one of the two non-pressure based parameters indicates there is a lack of oil, the lubricant-out sensor 110 provides a signal that there is oil in the system. If both of the two non-pressure based parameters indicate there is a lack of oil, the lubricant-out sensor 110 provides a signal that there is a lack oil in the system. In this way, the combination of sensing elements 136, 137, 138 provide independent measurements to reliably detect a lack of oil in the system.

In still further accordance with an exemplary embodiment, lubricant flowing through second lubricant return passage 96 contacts the plurality of sensing elements 133. A signal representing a non-pressure based parameter of the lubricant is sent from lubricant-out sensor 110 to controller 129. In the event that lubricant-out sensor 110 fails to detect the non-pressure based parameter, a determination is made in controller 129 that an issue may exist in first gearbox 35. For example, housing 60 may have been compromised resulting in a loss of lubricant. Controller 129 outputs an alert that is received by personnel controlling aircraft 10 via a display 144. The alert may also take the form of an audible warning issued through a speaker 146. The personnel may represent pilots in aircraft 10 or ground based controllers. The alert establishes a starting point for the loss of lubricant.

The personnel may then determine a time frame for landing aircraft 10 before first gearbox 35 fails.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A gearbox comprising:
   a housing including a lubricant reservoir;
   at least one gear system arranged in the housing;
   at least one lubricant delivery passage operable to direct a flow of lubricant from the lubricant reservoir onto the at least one gear system;
   at least one lubricant return passage defined completely within the housing and operable to guide the flow of lubricant from the at least one gear system to the lubricant reservoir; and
   a lubricant-out sensor fluidically connected to the at least one lubricant return passage, the lubricant-out sensor being operable to detect a loss of lubricant based on a non-pressure based parameter of lubricant in the gearbox.

2. The gearbox according to claim 1, wherein the lubricant-out sensor includes a sensing element extending into the at least one lubricant return passage.

3. The gearbox according to claim 1, wherein the lubricant-out sensor comprises a temperature sensor, wherein the non-pressure based parameter of the lubricant in the gearbox comprises lubricant temperature.

4. The gearbox according to claim 1, wherein the lubricant-out sensor comprises a conductivity sensor, wherein the non-pressure based parameter of the lubricant in the gearbox comprises lubricant conductivity.

5. The gearbox according to claim 1, wherein the lubricant-out sensor comprises a combination sensor operable to sense at least two non-pressure based parameters of the lubricant in the gearbox.

6. The gearbox according to claim 5, wherein the at least two non-pressure based parameters of the lubricant in the gearbox include temperature and conductivity.

7. The gearbox according to claim 1, wherein the gearbox comprises a splash lubricated gearbox.

8. A rotary wing aircraft comprising:
   an airframe including an extending tail;
   at least one engine operatively supported to the airframe;
   a main rotor assembly operatively coupled to the at least one engine;
   a tail rotor assembly mounted at the extending tail;
   at least one gearbox operatively connecting the at least one engine and the tail rotor assembly, the gearbox comprising:
      a housing including a lubricant reservoir;
      at least one gear system arranged in the housing;
      at least one lubricant delivery passage operable to direct a flow of lubricant from a lubricant reservoir onto the at least one gear system;
      at least one lubricant return passage defined completely within the housing and operable to guide the flow of lubricant from the at least one gear system to the lubricant reservoir; and
      a lubricant-out sensor fluidically connected to the at least one lubricant return passage, the lubricant-out sensor being operable to detect a loss of lubricant based on a non-pressure based parameter of a lubricant in the gearbox.

9. The rotary wing aircraft according to claim 8, wherein the lubricant-out sensor comprises a temperature sensor, wherein the non-pressure based parameter comprises a temperature parameter.

10. The rotary wing aircraft according to claim 8, wherein the lubricant-out sensor comprises a conductivity sensor, wherein the non-pressure based parameter comprises a conductivity parameter.

11. The rotary wing aircraft according to claim 8, wherein the lubricant-out sensor comprises a combination sensor operable to sense at least two non-pressure based parameters of the lubricant.

12. The rotary wing aircraft according to claim 11, wherein the at least two non-pressure based parameters include temperature and conductivity.

13. The rotary wing aircraft according to claim 8, wherein the gearbox comprises a splash lubricated gearbox.

14. The rotary wing aircraft according to claim 8, further comprising a controller connected to the lubricant-out sensor and which sends an alert when the lubricant-out sensor detects a loss of lubricant based on the non-pressure based parameter of the lubricant in the gearbox, and a display which displays a lubricant out warning based on the alert sent from the controller.

15. The rotary wing aircraft according to claim 14, wherein the non-pressure based parameter includes at least one of a temperature parameter and a conductivity parameter.

* * * * *